United States Patent
Flaig

(10) Patent No.: US 7,162,140 B2
(45) Date of Patent: Jan. 9, 2007

(54) MONITORING AN OPTICAL ELEMENT OF A PROCESSING HEAD OF A MACHINE FOR THERMAL PROCESSING OF A WORKPIECE

(75) Inventor: Rainer Flaig, Eschbronn (DE)

(73) Assignee: Trumpf Laser GmbH + Co. KG, Schrumberg (DE)

(*) Notice: Subject to any disclaimer, the term of this patent is extended or adjusted under 35 U.S.C. 154(b) by 0 days.

(21) Appl. No.: 10/892,399

(22) Filed: Jul. 16, 2004

(65) Prior Publication Data

US 2006/0012783 A1  Jan. 19, 2006

(51) Int. Cl.
*G02B 6/00* (2006.01)
*G01N 21/88* (2006.01)

(52) U.S. Cl. .................... 385/147; 356/237.1
(58) Field of Classification Search ......... 385/147; 356/239.1–239
See application file for complete search history.

(56) References Cited

U.S. PATENT DOCUMENTS 6,100,971 A * 8/2000 Imaino et al. ......... 356/237.2
6,118,527 A   9/2000 Jurca
6,370,171 B1 * 4/2002 Horn et al. ............. 372/34
2004/0008342 A1 * 1/2004 Hutt et al. ........... 356/239.1
2004/0240493 A1 * 12/2004 Uto et al. ............... 372/22

FOREIGN PATENT DOCUMENTS

| DE | 195 07 401 | 10/1995 |
| DE | 196 05 018 | 8/1997 |
| DE | 101 08 955 | 10/2002 |
| DE | 101 13 518 | 10/2002 |
| DE | 101 30 875 | 1/2003 |
| JP | 59-27793 | 2/1984 |

* cited by examiner

Primary Examiner—Sung Pak
Assistant Examiner—Tina M. Wong
(74) Attorney, Agent, or Firm—Fish & Richardson P.C.

(57) ABSTRACT

An apparatus for monitoring soiling of an optical element of a processing head of a machine for laser processing of a workpiece includes a first transparent optical element, positioned in a path of a laser beam, a second transparent optical element, positioned in the path of a laser beam and separated from the first transparent optical element by a gap, a first detector for detecting laser light scattered from the first transparent optical element, and a second detector for detecting laser light scattered within the gap between the first transparent optical element and the second transparent optical element.

29 Claims, 2 Drawing Sheets

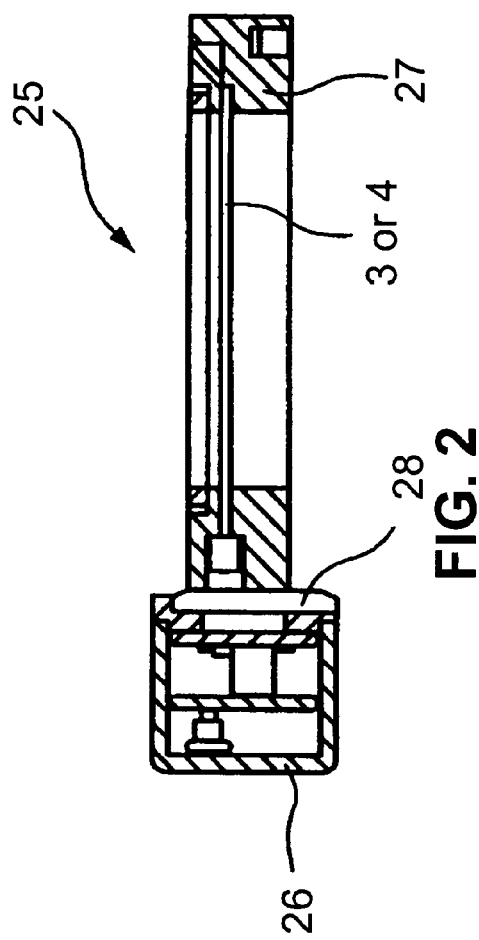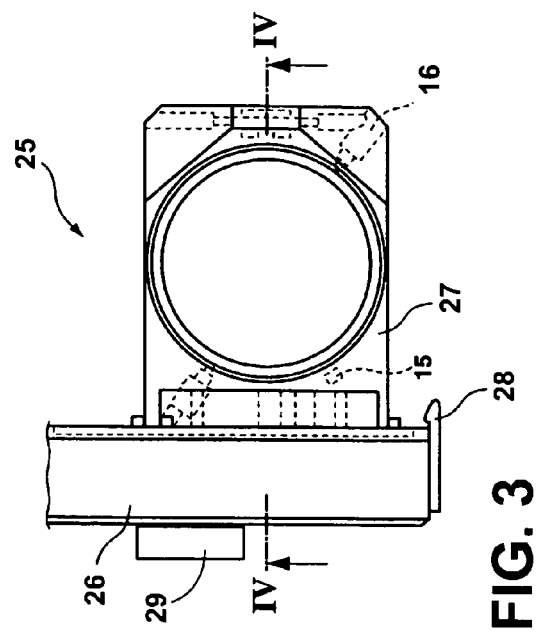

MONITORING AN OPTICAL ELEMENT OF A PROCESSING HEAD OF A MACHINE FOR THERMAL PROCESSING OF A WORKPIECE

TECHNICAL FIELD

This invention relates to thermal processing machines and, in particular, to monitoring an optical element of a processing head of a machine for thermal processing of a workpiece.

BACKGROUND OF THE INVENTION

German patent number DE 195 07 401 A1 discloses monitoring soiling of a protective glass through reference measurement on a first optical element and measurement of a soiled second optical element.

During the processing of workpieces with a machine for thermal welding or cutting, (e.g., a laser processing machine) splashes and smoke are produced in the processing region of the workpiece. The splashes and smoke may be deposited on a surface of an optical element that faces the workpiece of the processing head of the machine and may soil the surface of the optical element. The splashes may be burnt into the optical surface. Smoke can be deposited on the optical surface but can be removed from the optical surface to a certain extent. Deposits on or damage to the optical surface can result in an increased absorption of the laser radiation by the optical element. Accordingly, the thermal load of the optical element increases, which results in a noticeable decrease of the laser power available in the processing region. In case of heavy soiling, in particular, through splashes, increased absorption of the laser radiation can result in the destruction of the optical element.

For this reason, it is necessary to detect splashes or smoke on the optical element at an early stage to ensure constant thermal power in the working region of the workpiece and prevent destruction of the optical element by switching off the thermal processing machine in due time or to indicate that cleaning or replacement of the optical element is required.

German patent number DE 195 07 401 C2 discloses the detection and linear evaluation of stray light on the protective glass edge. A reference measured value is generated by measuring the stray light also on an additional transmitting element located in the beam path. In this manner, the influence of the laser power on the measuring signal can be compensated. Disturbances through reverse reflection from the workpiece, welding flares, external light etc., however, disturb the evaluation signal, because these disturbances affect only the protective glass and not the element providing the reference. The linear evaluation may cause problems with regard to overloading or underloading during evaluation. Detection of soiling through smoke in this way may be inaccurate because smoke produces only very little stray light on the protective glass edge.

SUMMARY OF THE INVENTION

The invention relates generally to an apparatus and method for the detection of soiling of an optical element of a processing head of a machine for thermal processing of a workpiece.

Monitoring an optical element of a processing head of a machine for thermal processing of a workpiece (e.g., a laser processing machine) can be achieved through detection of stray light on the optical element and detection of stray light on an additional, neighboring optical element for reference. Detection of the stray light can be provided in a gap between the first and the second optical element. Soiling through splashes and smoke can be detected, as the presence of stray light in the gap indicates the formation of smoke on the optical surface of the optical element.

Stray light can be measured and compared to the reference light using a logarithmic scale. Use of a logarithmic scale in connection with the use of an additional optical element for reference can have the following advantages. Logarithmic stray light detection permits detection and evaluation of stray light signals over a range of more than 5 decades (100 dB), which permits reliable detection of laser power signals in the Watt to kilowatt range and affords detection of different types of soiling and "additive" disturbing variables, such as, for example, reverse reflection, and welding flares.

A clean protective cover glass can be located near an optical element of the processing head. For example, the cover glass can be located close to an optical element in the laser beam path (e.g., a focusing lens of the processing head) that can act as the first optical element and that can serve as a measuring signal reference. The additional (second) optical element can be traversed by all relevant light beams (e.g., the laser light from the processing head, reflected laser light, and welding flares) that likewise traverse the soiled optical element. The signal on the additional optical element can also be detected with a photo diode and can be evaluated logarithmically.

A cartridge can be provided for holding the optical elements, and the cartridge can be plugged into and unplugged from a processing head of the machine. The detector can also be mounted to the cartridge. Such an arrangement facilitates exchange of the optical element and/or associated monitoring elements. Connecting bores in the cartridge between the optical elements and the detectors are closed by glass plugs to prevent dirt or dust particles from entering the cartridge.

Electronics for evaluation of the intensity of the scattered light beam can also be disposed on the cartridge, which reduces the susceptibility of the apparatus to mechanical and electrical disturbances and reduces cable lengths in the apparatus. The electronics can also include a storage medium for storing correction and calibration data.

Optical elements, the detector, and the electronics for signal evaluation can form one modular unit, which is housed in the form of a structural component on or in the cartridge, and can thereby be removed or supplied to the processing head in the form of a calibrated module. When the module is plugged in, the required electrical or mechanical contacts are automatically established through plug connections.

In a first general aspect, an apparatus for monitoring soiling of an optical element of a processing head of a machine for laser processing of a workpiece includes a first transparent optical element, positioned in a path of a laser beam, a second transparent optical element, positioned in the path of a laser beam and separated from the first transparent optical element by a gap, a first detector for detecting laser light scattered from the first transparent optical element, and a second detector for detecting laser light scattered within the gap between the first transparent optical element and the second transparent optical element.

Implementations can include one or more of the following features. For example, the apparatus can further include a processor for providing a first signal proportional to a logarithm of an intensity of light detected by the first detector, a processor for providing a second signal proportional to a logarithm of an intensity of light detected by the second detector, and a micro-controller for comparing the first signal and the second signal. A difference between the first signal and the second signal can be proportional to the amount of smoke on a surface of the second optical element. The apparatus can include a cartridge adapted for holding the second optical element and adapted for plugging into and unplugging from the processing head of the machine for laser processing of a workpiece, and the cartridge can include a display for displaying a signal proportional to the amount of smoke on a surface of the second optical element.

The apparatus can further include a third detector for detecting laser light scattered from the second transparent optical element. The apparatus can include a processor for providing a first signal proportional to a logarithm of an intensity of laser light detected by the first detector, a processor for providing a third signal proportional to a logarithm of an intensity of laser light detected by the third detector, and a micro-controller for comparing the first signal and the third signal. A difference between the first signal and the third signal can be proportional to the level of soiling of the surface of the second transparent optical element. The apparatus can include a cartridge adapted for holding the second optical element and adapted for plugging into and unplugging from the processing head of the machine for laser processing of a workpiece, and the cartridge can include a display for displaying a signal proportional to a level of soiling of the second optical element.

In another general aspect, a method of detecting soiling of an optical element of a processing head of a machine for laser processing of a workpiece includes shining a laser beam through a first transparent optical element and a second transparent optical element, where the first transparent optical element and the second transparent optical element are separated by a gap, detecting laser light scattered from the first transparent optical element with a first detector, detecting laser light scattered within the gap between the first transparent optical element and the second transparent optical element with a second detector, and comparing an intensity of light detected by the first detector with an intensity of light detected by the second detector.

Implementations can include one or more of the following features. The method can further include providing a first signal proportional to a logarithm of an intensity of light detected by the first detector, providing a second signal proportional to a logarithm of an intensity of light detected by the second detector, and comparing the first signal and the second signal. A difference between the first signal and the second signal can be proportional to an amount of smoke on the second optical element. The method can further include displaying a detected amount of smoke on a display. The amount of smoke on the second optical element can be proportional to the difference between an intensity of light detected by the first detector with an intensity of light detected by the second detector, and the method can further include generating an alert when an amount of smoke on the second optical element exceeds a predetermined value.

The method can further include detecting laser light scattered from a surface of the second transparent optical element with a third detector and comparing an intensity of light detected by the first detector with an intensity of light detected by the third detector. The method can further include providing a first signal proportional to a logarithm of an intensity of light detected by the first detector, providing a third signal proportional to a logarithm of an intensity of light detected by the third detector, and comparing the first signal and the third signal. A difference between the first signal and the third signal can be proportional to the level of soiling of the surface of the second transparent optical element. The method can further include displaying a detected level of soiling of the second optical element on a display. A level of soiling on the second optical element can be proportional to the difference between an intensity of light detected by the first detector with an intensity of light detected by the third detector, and further comprising generating an alert when a level of soiling exceeds a predetermined value.

An optical element as defined herein can include focusing lens, a protective glass, or a window of the processing head.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF DRAWINGS

FIG. 2 is a longitudinal section through a cartridge for holding the protecting glass of a laser processing machine.

FIG. 3 is a top view of the cartridge of FIG. 2.

Like reference symbols in the various drawings indicate like elements.

DETAILED DESCRIPTION

Figure 1:
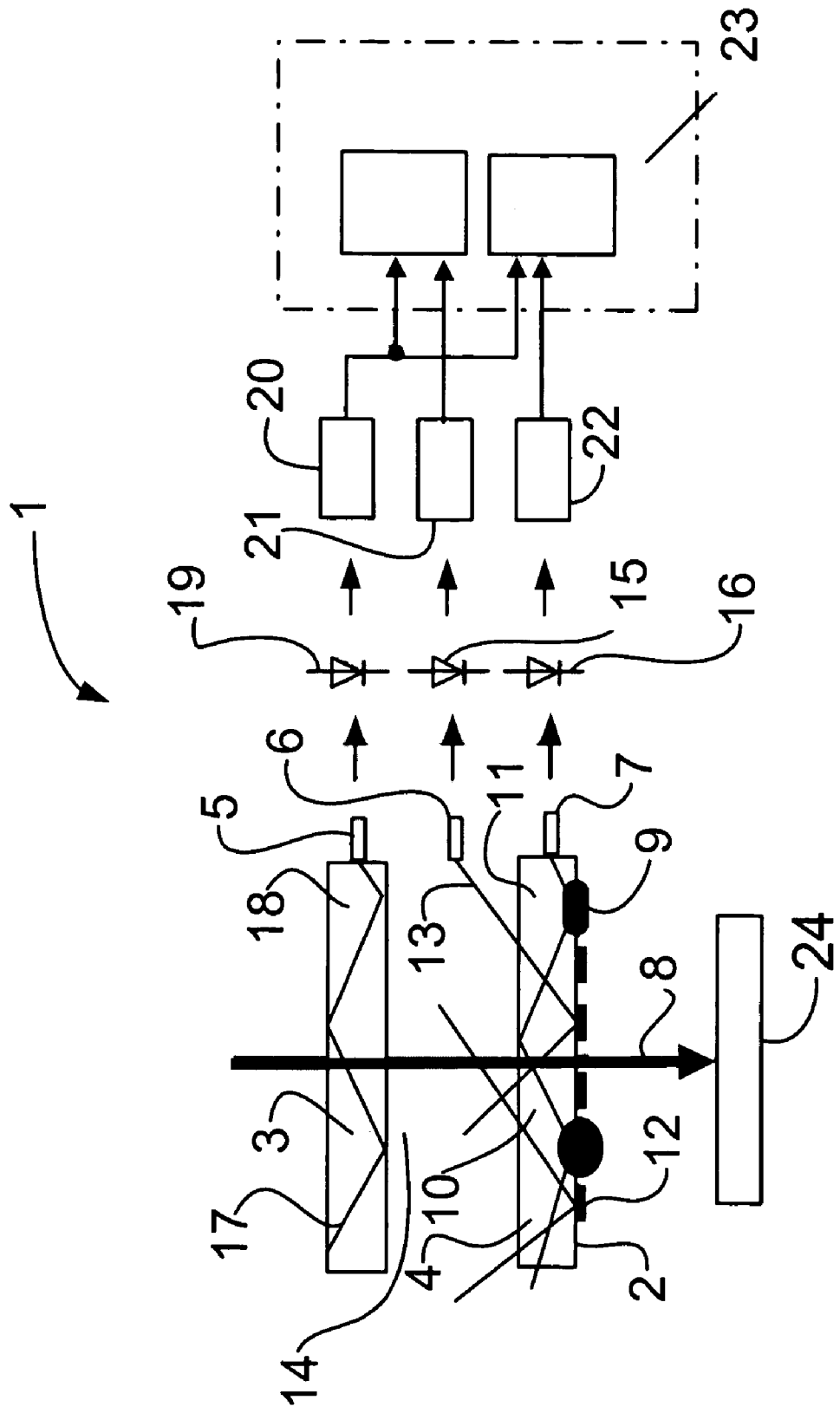
FIG. 1 is a schematic side view of an apparatus for detecting soiling of an optical element.

As is shown in FIG. 1, an apparatus 1 for monitoring the soiling of an optical surface 2 includes a first protective glass 3, a second protective glass 4, three glass plugs 5, 6, and 7, and three sensors 15, 16, and 19 for detecting stray light. The optical elements of the apparatus 1 (i.e., the first protective glass 3 and the second protective glass 4) can be flat slides but can also be lenses, partially-reflecting mirrors or other optical elements. The protective glasses 3 and 4 can be held in a cartridge such that they can be easily exchanged by the operator (as explained in more detail below).

A focused laser beam 8 emitted by a processing head (not shown) of a laser processing machine impinges on a workpiece 24 for processing the workpiece. During processing of the workpiece 24, the second protective glass 4 can be soiled, which results in reduced laser beam power reaching the workpiece 24 and decreased processing of the workpiece 24. If processing of the workpiece 24 continues despite the soiling, further components of the processing head can be subjected to an increased load if constant power is maintained on the workpiece.

The intensity of stray light scattered from optical elements 3 and 4 can be measured and used to evaluate the degree or level of soiling. Downstream electronics can use the measurements to interrupt processing of the workpiece 24 when a predetermined value indicative of a certain amount of soiling has been exceeded and can alert a user that exchange or cleaning of the second protective glass 4 is required.

Soiling of the optical elements 3 and 4 can be produced through splashes or smoke of material ejected from the workpiece 24. Splashes of material 9 can be produced and deposited on the optical surface 2 of the second protective glass 4 and partially burnt into the optical surface 2. The splashes 9 generate stray scattered light 10, which mainly exits the optical elements 3 and 4 at the protective glass edge 11. Smoke 12 can also be deposited on the optical surface 2 with the consequence that stray light 13 enters mainly into the optical gap 14 between the first protective glass 3 and the second protective glass 4.

The intensity of stray light at the protective glass edge 11 and in the gap 14 is detected to monitor the soiling. To this end, the intensity is measured by photo diodes 15 and 16. The path between the protective glass edge 11 and the detectors 16 is closed by glass plug 7 to prevent dirt or dust particles from entering. A small gap of approximately 0.2 mm has to remain between the glass plug 7 and the protective glass edge 11 to prevent scratching of the plug 7 or of the protective glass edge 11. The photo diodes 15 and 16 and the evaluation circuit can also be integrated into the cartridge that holds the optical elements.

The performance and evaluation of the protective glass monitoring includes, in addition to detection of stray light 10 and 13, the detection of the stray light 17 coupled into the first protective glass 3 on the first clean protective glass 3. The second protective glass 4, the region above the second protective glass 4, and the first protective glass 3 are monitored.

The stray light is detected by sensors at at least three different locations: (1) on the edge 18 of the first protective glass 3, which provides a reference signal; (2) on the protective glass edge 11 of the second protective glass 4, for monitoring of splashes; and (3) above the second protective glass 4 between the first protective glass 3 and the second protective glass 4, for monitoring of smoke. The three-fold measurement permits monitoring of the degree or level of soiling of the protective glass 4, the type of soiling (e.g., splashes or smoke), and the soiling of the region of fiber coupling.

Depending on the degree of soiling, laser power, disturbing light, and reverse reflection, the intensity levels measured at the different locations increase differently. The signals generated by the photo diodes 15 and 16 and by a photo diode 19 for the stray light 17 on the first protective glass 3 are evaluated by processors 20, 21, and 22 to produce a signal proportional to the logarithm of the directly measured light intensities. The photo diode current signals are logarithmically detected and converted into a voltage by the processors 20, 21, and 22. The logarithmic signals are evaluated by comparing them, for example in a microcontroller 23.

The light levels can be processed over a range of more than 100 dB (5 decades) due to the large signal range of the logarithmic evaluation. The mutual ratio of the signals can be determined from the differences of the individual logarithmic signals.

The amount of smoke present on the surface of the protective glass 4 can be determined by subtracting the log of the stray light intensity in the gap 14 (the "gap signal"), measured with photo diode 15, from the log of the reference light intensity at the edge 18 of protective glass 3 (the "reference signal"), measured with photo diode 19. Thus, the amount of smoke is proportional to log(gap signal)−log(reference signal)=log(gap signal/reference signal).

The amount of material 9 splashed onto the surface 2 of the protective glass 4 can be determined by subtracting the log of the intensity of stray light scattered by material in the splashed material 9 (the "optical surface signal"), measured with photo diode 16, from the log of the reference signal. Thus, the amount of splashed material 9 is proportional to log(optical surface signal)−log(reference signal)=log(optical surface signal/reference signal). The difference of the log signals and the log of the ratio of signals indicates the degree or level of soiling, and measurements have shown that the "logarithmized ratio" correlates well with the degree of soiling.

Although individual signal variations, caused by back reflections, variations of laser power, external ambient light, etc. affect the signal recorded by the photo diodes 15, 16, and 19, the ratio of the signals, and therefore the protective glass monitoring, is only slightly affected by such signal variations. Thus, the degree of soiling and the type of soiling (e.g., smoke or splashes/burning in) can be detected over a large range of laser power (e.g., from Watts to tens of kilowatts). The comparison of the signals measured at photo diodes 15 and 16 with the reference signal measured at photo diode 19 renders the measured values largely stable compared to the mentioned disturbing variables and the laser power.

Referring to FIG. 2 and FIG. 3, to facilitate replacement of a protecting glass 3 or 4, a cartridge 25 is provided that can be inserted into the processing head. The cartridge 25 includes a cartridge head 26 for convenient insertion and removal of the cartridge 25 and a cartridge insert 27 for holding the protecting glass 3 or 4. The cartridge insert 27 is characterized by a holder that includes a circular mounting or frame for the protecting glass 3 or 4. Only the protecting glass edge is supported on the mounting such that the protecting glass 3 or 4 is almost completely transparent for light beams. The protecting glass 3 or 4 can be inserted into the cartridge insert 27 and removed again. For stationary fixing of the protecting glass 3 or 4, a pivotable flap is provided for clamping the lateral protecting glass edge. Photo diodes 15, 16 and 19 can be adjustably positioned on the cartridge insert. The overall unit 25 can be inserted into and withdrawn from the processing head of the laser processing machine. The cartridge 25 can be inserted up to the cartridge head 26. A safety device in the form of a locking lever 28 locks the inserted cartridge 25 in a cavity of the processing head.

The degree of soiling of the protective glass 4 can be directly displayed through a display 29 (e.g., an LED light display) located on the protective glass cartridge. Alternatively, the evaluated signals can be transmitted to the laser control and are displayed in an operating program of the laser.

OTHER EMBODIMENTS

A number of embodiments of the invention have been described. Nevertheless, it will be understood that various modifications may be made. Accordingly, other embodiments are within the scope of the following claims.

What is claimed is:

1. An apparatus for monitoring soiling of an optical element of a processing head of a machine for laser processing of a workpiece, the apparatus comprising:

a first transparent optical element, positioned in a path of a laser beam;

a second transparent optical element, positioned in the path of a laser beam and separated from the first transparent optical element by a gap;

a first detector for detecting laser light scattered from the first transparent optical element and for providing a reference signal; and a second detector for detecting laser light scattered within the gap between the first transparent optical element and the second transparent optical element and for providing a gap signal.

2. The apparatus of claim 1, further comprising a processor for providing a first signal proportional to a logarithm of an intensity of light corresponding to the reference signal provided by the first detector.

3. The apparatus of claim 2, further comprising a processor for providing a second signal proportional to a logarithm of an intensity of light corresponding to the gap signal provided by the second detector.

4. The apparatus of claim 3, further comprising a microcontroller for comparing the first signal and the second signal.

5. The apparatus of claim 4, wherein a difference between the first signal and the second signal is proportional to the amount of smoke on a surface of the second optical element.

6. The apparatus of claim 1, further comprising a cartridge adapted for holding the second optical element and adapted for plugging into and unplugging from the processing head of the machine for laser processing of a workpiece.

7. The apparatus of claim 6, wherein the cartridge includes a display for displaying a signal proportional to the amount of smoke on a surface of the second optical element.

8. The apparatus of claim 1, further comprising a third detector for detecting laser light scattered from the second transparent optical element and for providing an optical surface signal.

9. The apparatus of claim 8, further comprising a processor for providing a first signal proportional to a logarithm of an intensity of laser light corresponding to the reference signal provided by the first detector.

10. The apparatus of claim 9, further comprising a processor for providing a third signal proportional to a logarithm of an intensity of laser light corresponding to the optical surface signal provided by the third detector.

11. The apparatus of claim 10, further comprising a micro-controller for comparing the first signal and the third signal.

12. The apparatus of claim 11, wherein a difference between the first signal and the third signal is proportional to a level of soiling of a surface of the second transparent optical element.

13. The apparatus of claim 8, further comprising a cartridge adapted for holding the second optical element and adapted for plugging into and unplugging from the processing head of the machine for laser processing of a workpiece.

14. The apparatus of claim 13, wherein the cartridge includes a display for displaying a signal proportional to a level of soiling of the second optical element.

15. A method of detecting soiling of an optical element of a processing head of a machine for laser processing of a workpiece, the method comprising:

shining a laser beam through a first transparent optical element and a second transparent optical element, wherein the first transparent optical element and the second transparent optical element are separated by a gap;

detecting laser light scattered from the first transparent optical element with a first detector and providing a reference signal;

detecting laser light scattered within the gap between the first transparent optical element and the second transparent optical element with a second detector and providing a gap signal; and comparing an intensity of light detected by the first detector corresponding to the reference signal with an intensity of light detected by the second detector corresponding to the gap signal.

16. The method of claim 15, further comprising:

providing a first signal proportional to a logarithm of an intensity of light corresponding to the reference signal provided by the first detector;

providing a second signal proportional to a logarithm of an intensity of light corresponding to the gap signal provided by the second detector; and comparing the first signal and the second signal.

17. The method of claim 16, wherein a difference between the first signal and the second signal is proportional to an amount of smoke on the second optical element.

18. The method of claim 17, further comprising displaying a detected amount of smoke on a display.

19. The method of claim 15, wherein an amount of smoke on the second optical element is proportional to the difference between an intensity of light corresponding to the reference signal provided by the first detector with an intensity of light corresponding to the gap signal provided by the second detector, and further comprising generating an alert when an amount of smoke on the second optical element exceeds a predetermined value.

20. The method of claim 15, further comprising:

detecting laser light scattered from a surface of the second transparent optical element with a third detector and providing an optical surface signal; and comparing an intensity of light corresponding to the reference signal provided by the first detector with an intensity of light corresponding to the optical surface signal provided by the third detector.

21. The method of claim 20, further comprising:

providing a first signal proportional to a logarithm of an intensity of light corresponding to the reference signal provided by the first detector;

providing a third signal proportional to a logarithm of an intensity of light corresponding to the optical surface signal provided by the third detector; and comparing the first signal and the third signal.

22. The method of claim 21, wherein a difference between the first signal and the third signal is proportional to the level of soiling of the surface of the second transparent optical element.

23. The method of claim 22, further comprising displaying a detected level of soiling of the second optical element on a display.

24. The method of claim 15, wherein a level of soiling on the second optical element is proportional to the difference between an intensity of light corresponding to the reference signal provided by the first detector with an intensity of light corresponding to the optical surface signal provided by the third detector, and further comprising generating an alert when a level of soiling exceeds a predetermined value.

25. An apparatus for monitoring soiling of an optical element of a processing head of a machine for laser processing of a workpiece, the apparatus comprising:

a first transparent optical element, positioned in a path of a laser beam;

a second transparent optical element, positioned in the path of a laser beam and separated from the first transparent optical element by a gap;
a first detector for detecting laser light scattered from the first transparent optical element and for providing a reference signal; and
a second detector for detecting laser light scattered from the second transparent optical element and for providing an optical surface signal.

26. The apparatus of claim 25, further comprising a processor for providing a first signal proportional to a logarithm of an intensity of light corresponding to the reference signal provided by the first detector.

27. The apparatus of claim 26, further comprising a processor for providing a second signal proportional to a logarithm of an intensity of light corresponding to the optical surface signal provided by the second detector.

28. The apparatus of claim 25, further comprising a micro-controller for comparing the first signal and the second signal.

29. The apparatus of claim 28, wherein a difference between the first signal and the second signal is proportional to an amount of soiling on a surface of the second optical element.

* * * * *